United States Patent [19]

Suer

[11] Patent Number: 5,225,194

[45] Date of Patent: Jul. 6, 1993

[54] AQUEOUS DIAFILTRATION PROCESS FOR PREPARING ACELLULAR VACCINES, AGAINST SELECTED BACTERIAL DISEASES

[75] Inventor: Lynn D. Suer, Castro Valley, Calif.

[73] Assignee: LDC Research Corporation, San Leandro, Calif.

[21] Appl. No.: 435,335

[22] Filed: Nov. 13, 1989

[51] Int. Cl.$^5$ .............................................. A61K 39/02
[52] U.S. Cl. ........................................ 424/92; 424/88;
514/54; 530/350; 530/395; 530/806; 530/825;
530/419
[58] Field of Search ...................... 514/54; 424/92, 88;
536/123, 127; 530/419, 350, 395, 806, 825

[56] References Cited

U.S. PATENT DOCUMENTS

| | | | |
|---|---|---|---|
| 3,636,192 | 1/1972 | Gotschlich | 424/92 |
| 4,123,520 | 10/1978 | Hagopian | 424/92 |
| 4,298,597 | 11/1981 | Acres et al. | 424/92 |
| 4,753,796 | 6/1988 | Moreno et al. | 424/92 |
| 4,755,381 | 7/1988 | Cryz | 424/92 |
| 4,877,613 | 10/1989 | Vedros et al. | 424/92 |

FOREIGN PATENT DOCUMENTS 0088303  3/1982  European Pat. Off. ............... 424/92

OTHER PUBLICATIONS

Adlam D. C., et al. 1984, Journal of Gen. Microbiology 130: 2415–2426.
Gotschlich, E. C. 1975, Monogr. Allergy 9: 245–258.
Hall, Richard F., et al. 1977, Vet. Med./Small Animal Clinician 72: 1368–1370.
McKinney, K. L., et al. 1985, Vet. Microbio. 10: 465–480.
Rosendal, S., et al. 1986, Vet. Microbio. 12: 229–240.
Vedros, N. A., et al., 13th Ann. Conf. and 7th Eastern Fish Health Workshop, Baltimore, Maryland, May 9–13, 1982.
Vedros, N. A., et al. 1988, Diseases of Aquatic Organisms 5: 157–161.
Vedros, N. 1976, WHO Techn. Report Series No. 588.
Knox, K. W., et al. 1960, Immunology 3: 352–362.

*Primary Examiner*—Jeffrey E. Russel
*Assistant Examiner*—P. Lynn Touzeau
*Attorney, Agent, or Firm*—James C. Weseman

[57] ABSTRACT

Immunogenic components are recovered from pathogenic bacteria grown on semi-defined, serum-free media in purified forms that are useful as veterinary acellular vaccines and include both polysaccharides as well as proteins. Recovery is accomplished by homogenizing the cells; precipitating unwanted cellular compounds such as nucleic acids using a quaternary ammonium salt to form insoluble ionic complexes; treating the resulting supernatant with a hypersaline solution to dissociate any residual ionic complexes; and concentrating and dialyzing the supernatant to remove the ammonium and chloride salts and various unwanted components derived from the culture medium.

19 Claims, No Drawings

AQUEOUS DIAFILTRATION PROCESS FOR PREPARING ACELLULAR VACCINES, AGAINST SELECTED BACTERIAL DISEASES

TECHNICAL FIELD

The present invention relates to veterinary medicine and microbiology. More specifically, the invention is directed to a method for providing inexpensive and reliable acellular vaccines against a variety of bacterial pathogens in animals.

BACKGROUND OF THE INVENTION

Bacterial pathogens are a common cause of serious disease in farm animals and household pets. The majority of such diseases are caused by various bacterial species, including but not limited to *Pasteurella multocida, P. haemolytica, Haemophilus somnus, H. pleuropneumoniae, Bordetella bronchiseptica, Moraxella bovis,* and *Erysipelothrix rhusiopathiae*. Standard vaccines for these disease fall into a class of vaccines called bacterins, which are inactivated or attenuated whole organism preparations. The efficacy of bacterins, however, has been questioned. See, e.g., Hall, R. F., et al, 1977, Vet. Med. Small Animal Clin. 72: 1368-1370. Moreover, the immune response to bacterins is generally short-lived and is not directed to specific cellular constituents associated with the virulence of the microorganism.

One possible alternative to bacterins is production of a vaccine based upon specific immunogenic components isolated from the pathogenic organism. Although the isolation of specific bacterial components is well known in the art, economical and practical veterinary vaccines based on such components have not been thought possible. See, for example, Rosendal et al. (1986, Vet. Microbiol. 12: 229-240) who describe a process of bacterial cell extraction from *Haemophilus pleuropneumonia* using sodium chloride and Cetavalon (hexadecyltrimethyl ammonium bromide) but conclude that such extractions are not sufficiently efficacious as a vaccine to warrant field use. Other work on acellular vaccines include Adlam et al. (1984, J. Gen. Microbiol. 130: 2415-2426, describing a process for obtaining purified capsular polysaccharide by a series of alcohol and acetone extractions) and McKinney et al. (1985, Vet. Microbiol. 10: 465-480, describing a process of saline extraction of the bacteria followed by separation of heterogenous protein components by preparative and analytical isoelectrofocusing).

Vedros et al. (1982, 13th Ann. Conf. Aquatic Animal Med.) reported preparation of an acellular vaccine for pasteurellosis (*Pasteurella multocida*) in marine mammals. That process comprised shearing away surface components of the cell with glass beads; precipitation of the components using ammonium sulfate; removal of proteins using enzymes and alkaline hydrolysis; and separation of the polysaccharide components through alcohol precipitation, molecular sieving and ion exchange chromatography. A modification of this process was used to produce an acellular vaccine for melioidosis (*Pseudomonas pseudomallei*) in marine mammals (Vedros et al., 1988, Dis. Aquatic Org. 5: 157-161). Further, U.S. patent application No. 07/081,942, filed Aug. 5, 1987, now U.S. Pat. No. 4,877,613, describes a process for preparing acellular vaccines against gram negative non-enteric pathogenic bacilli, in which surface and cellular polysaccharides are mechanically sheared away, followed by precipitation with Cetavalon, removal of nucleic acids with alcohol, and then further precipitated with alcohol yielding "Formulation I." The supernatant of the Cetavalon precipitation was further treated with alcohol to yield "Formulation II." The preferred vaccine was derived from a mixture of Formulations I and II.

In the area of human medicine, acellular vaccine preparations are known, but are derived through complicated and expensive procedures. Such vaccines have been disclosed in U.S. Pat. Nos. 3,636,192 to Gotschlich; No. 4,753,796 to Moreno; and No. 4,755,381 to Cryz. Further examples can be found in Gotschlich, 1975, Monograph. Allergy 9: 245-258. These references disclose methods for obtaining specific cellular components which previous research has shown to be immunogenic, but require the use of quaternary ammonium salts in combination with alkanols to precipitate the desired polysaccharides. In cases where endotoxins are present, further extensive and complicated purification is necessary.

Although the art reveals certain known methods for preparing acellular vaccines, such methods are inadequate or unsatisfactory in one or more ways. Many of these techniques are complicated and expensive requiring many man hours to produce efficacious vaccines.

Another difficulty with known methods lies in the culture media of the bacterium of interest. Standard culture media include a wide array of components designed to foster abundant bacterial growth. Not only do such formulations tend to be expensive, and thereby add to vaccine cost, but they also include high molecular weight compounds such as animal sera that are very difficult to remove during vaccine purification. However, it is widely believed that such formulations are indispensable in order to ensure growth sufficient for vaccine production.

Known methods also require the use of large quantities of alkanols and other volatile compounds that are dangerous and costly to both store and use.

Finally, known methods of preparing acellular vaccines use live as opposed to killed microorgansims, necessitating laborious sterilization and isolation techniques as well as constant maintenance of cultures in order to ensure an adequate supply of fresh individuals.

SUMMARY OF THE INVENTION

It is an object of the present invention to provide an inexpensive method for making efficacious acellular vaccines for bacterial diseases in animals.

It is another object of this invention to provide a method of making acellular vaccines from formaldehyde-killed organisms.

It is a further object of the present invention to provide a method of making vaccines that does not rely on combustible, volatile organic compounds, such as alkanols.

It is yet another object of the present invention to provide culture media which allow adequate bacterial growth for effective vaccine production, but which do not include high molecular weight compounds that complicate or make vaccine purification difficult.

These and other objects are achieved by the invention disclosed and claimed herein. According to the present invention a method of acellular vaccine production from a late log-phase culture of bacteria is disclosed and comprises the following steps:

1. Inactivation of the bacteria with an aqueous solution of N formaldehyde to a final concentration of 0.15% v/v;
2. Homogenization of the culture and removal of the cells and insoluble particles by centrifugation;
3. Treatment of the supernatant with a mixed quaternary ammonium salt and removal of the precipitate by high speed centrifugation;
4. Treatment of the supernatant by mixing it with a 0.9 M sodium chloride solution; and
5. Concentration of the mixture produced in step four, followed by dialysis against double distilled water and filter sterilization.

The final product derived from this method may be either dried under a vacuum or maintained in liquid form.

Because production of the vaccine is accomplished from formaldehyde-inactivated as opposed to live organisms, the present method is much simpler and less involved. This is because the organisms are no longer pathogenic in their inactivated state. Thus, special precautions for maintaining decontamination and sterility of instruments and containers, as well as the isolation of the processing areas is obviated.

Another marked advantage of the present invention is that many immunogenic components, particularly in the cell membrane and extracellularly, are lost in standard techniques that focus almost entirely on surface components. Many of these additional components, such as cellular polysaccharides and extracellular proteins, are crucial in order to ensure a complete immunogenic response in the vaccinated individual.

Finally, the method of the present invention is superior to known methods because the use of alkanols and similar combustible, volatile organic compounds has been eliminated. In commercial scale vaccine production, very large quantities of alkanols are required presenting both storage and usage hazards. Indeed, the recent trend of vaccine manufacturers has been to refuse to use any vaccine production methods employing alkanols because of such safety considerations.

DETAILED DESCRIPTION OF THE INVENTION

This invention provides an aqueous diafiltration process for the isolation of an antigenic composition from formaldehyde-inactivated pathogenic bacteria. The composition consists of outer membrane polysaccharides and proteins, capsular polysaccharides, and extracellular components associated with virulence.

The term "capsular polysaccharide" intends the acidic extracellular polysaccharide which is excreted exterior of the cell membrane of the bacterium.

The term "outer membrane polysaccharide" intends the neutral polysaccharides of that are integrally associated with the cell membrane of the bacterium. Also referred to as "somatic polysaccharides."

The method of the present invention may be used to make veterinary vaccines against a broad array of bacterial species, including but not limited to *Moraxella bovis*, Haemophilus spp. such as *Haemophilus somnus*, Pasteurella spp. such as *Pasteurella hemolytica* and *Pasteurella multocida* groups A and D, and *Actinobacillus pleuropneumoniae*. The vaccine of the invention comprises a purified mixture of capsular polysaccharides, outer membrane polysaccharides and cellular and extracellular proteins.

The bacteria are grown aerobically at physiological temperatures on a suitable semi-defined growth medium. It has been found that certain inexpensive culture formulations can support adequate bacterial growth to make vaccine production feasible without including high molecular weight compounds such as animal sera. The special media of the present invention include "Casamino acid medium" (CAM), "Blood agar medium" (BAP), and "Yeast-Casamino Acid-Cystine medium" (YCC). The composition of CAM and YCC are given in Tables 1 and 2 respectively. BAP comprises a typical blood agar base, well known in the art and supplied by Difco Co., which contains 3% defibrinated sheep's red blood cells. The medium is heated to 56° C. to produce Chocolate Blood Agar.

TABLE 1

| Composition of Casamino Acid Medium ("CAM") | |
|---|---|
| Component | Concentration/l |
| Casamino acids (certified, as supplied by Difco) | 20.0 g |
| NaCl | 5.0 g |
| NaPO$_4$ (12 HOH) | 6.5 g |
| Thiamine PO$_4$ | — g |
| IsoVitaLex (supplied by Difco) | — g |
| Dextrose (50% solution) | 15.0 ml |
| Yeast extract (dialyzed, 15% solution) | 1.5 ml |
| pH (adjusted with NaOH) | 7.6–7.8 |

TABLE 2

| Composition of Yeast - Casamino Acid - Cystine Medium ("YCC") | |
|---|---|
| Component | Concentration/l |
| Casamino acids (technical) | 15.0 g |
| L-Cystine | 0.5 g |
| Glucose | 2.0 g |
| Sucrose | 2.5 g |
| Na$_2$SO$_3$ | 0.2 g |
| Potassium diphosphate | 4.0 g |
| pH (adjusted with NaOH) | 7.6–7.8 |

General aspects of culture, cultural conditions and growth characteristics of bacteria are well known in the art. See, e.g., Manual of Clinical Microbiology (1985) 4th Edition, American Society for Microbiology, which is incorporated herein by reference.

The culture including both bacteria and growth medium may be used directly in the process. It is important, however, that the culture have entered late-log phase to ensure best results for reproducible quality from batch to batch.

The first step of the process is to inactivate or kill the culture. A late log phase culture of a desired strain is administered with an aqueous solution of N formaldehyde to a final concentration of 0.15% v/v. After 24 hours, the bacteria are plated out on culture medium and incubated for 18 hours to test for inviability, which is indicated by an absence of culture growth. Upon a finding of inactivation, the bacteria are then ready for harvest.

In the next step, the harvested culture is homogenized gently for 10–20 minutes in an ice bath. Any remaining intact cells or cellular debris are removed by centrifugation. The resulting supernatant is then decanted off.

In the second step of the method of the present invention, the supernatant is treated with a 10% solution of mixed alkyltrimethyl ammonium bromide to a final concentration of 1.5% v/v. This treatment produces a precipitate comprised of an ionic complex of the ammonium salt and certain chemical constituents such as some types of polysaccharides and nucleic acids. The precipitate is separated from the supernatant by centrifugation or other means and then is discarded.

The supernatant remaining at the end of step two is then treated by adding a 0.9 M aqueous solution of sodium chloride in order to dissociate any remaining ionic complexes in solution.

In the fourth step, the sodium chloride-containing supernatant is concentrated to 1/10 of its original volume. The concentrate is dialyzed against double distilled water for 24 hours and then further purified by filter sterilization. The resulting purified mixture contains the desired immunogenic components and may be either dried under vacuum or used in liquid form.

The acellular vaccines of this invention may be administered in a conventional manner to animals that are susceptible to infection by the pathogenic bacterium that was used to prepare the vaccine. Normally, subcutaneous, intradermal, or intramuscular injection is employed. The initial inoculation will typically be about 0.1–0.5 g active ingredient per kg of body weight. Periodic boosters may be required to provide adequate protection against infection over prolonged time periods. The vaccine may be formulated in isotonic pyrogen free saline, ringer's solution or dextrose solution, all of which are well known in the art, and administered in these solutions or in an alternative adjuvant or carrier that permits slow release of the antigens.

EXPERIMENTAL

The following examples describe in more detail the general method and vaccine products discussed above. These examples are not intended to limit the scope of the invention in any manner.

EXAMPLE 1.1

Culture of *Haemophilus somnus*

A lyophilized culture of *Haemophilus somnus* strain P-51 was suspended in 0.5 ml of CAM. The suspension was spread on BP at a concentration of 0.1 ml per plate and the plates incubated for 18 hours at 37° C. The growth from these plates was resuspended in 0.5 ml per plate of CAM and spread on BAP at a concentration of 0.1 ml per plate. The pooled suspension growth was added to Trypticase Soy Broth, the composition of which is well known in the art, containing 6% lactose and was distributed in 2 ml aliquots and frozen at −70° C. These aliquots served as pre-seed stock.

A pre-seed frozen aliquot is thawed slowly, spread on BAP, incubated for 18 hours at 37° C. and purity of the colonies checked visibly. Random colonies were identified using gram stain and biochemical tests well known in the art. The plate growth is then harvested with TSB (5 ml per plate) and aliquots frozen at −70° C. to serve as seed stock.

One frozen aliquot of seed stock is then slowly thawed and spread on two plates of BAP at a concentration of 0.1 ml per plate. After 18 hours incubation at 37° C., the growth on each plate is suspended in 5 ml of CAM and the harvest of both plates inoculated into a one liter Erlenmeyer flask containing pre-warmed 500 ml of CAM. The one liter flask was slowly rotated at 100 rpm for 2 hrs at 37° C. The growth was checked for purity microscopically and by streaking on BAP and inoculating on thioglycollate medium using methods well known in the art.

Production and harvest of a late log phase culture of *H. somnus* is accomplished by obtaining 50 ml of inoculum produced from the seed stock and inoculating each of six 500 ml volumes of CAM in one liter Erlenmeyer flasks. The flasks are then gently rotated at 125 rpm for 6 hours in an incubator at 376° C. By such time, the growth will have an optical density of 0.5–0.7 at 520 nm, or approximately 10 bacteria per ml culture. The growth is then examined for purity by using well known gram stain techniques and by streaking on BAP followed by 18 hours of incubation at 37° C. The resulting growth, if pure, is then pooled for vaccine production.

EXAMPLE 1.2

Vaccine Preparation From *H. Somnus*

The pooled culture is first inactivated by adding N formaldehyde to the culture to a final concentration of 0.15%. After 24 hours, a sample of the culture is tested for viability by streaking on 3 plates of BAP at a concentration of 0.1 ml per plate and incubated for 18 hours at 37° C. Absence of growth is considered sufficient evidence that the formaldehyde treatment has been successful and that the organisms are non-viable.

Following inactivation with formaldehyde, the culture was homogenized gently for 10 to 20 minutes in a Vitris homogenizer, model M-1150, set at the no. 2 speed for small scale, in an ice bath. Cells and debris were separated from the supernatant by high speed centrifugation at 7,000×g, and then discarded. A 10% (weight by volume) solution of mixed alkyltrimethyl ammonium bromide was then added to the supernatant to a final concentration of 1.5% v/v. After 3 hours setting at room temperature (21°–23° C.) the precipitate was separated by centrifugation (16,000×g at 4° C.) and discarded. To the resulting supernatant was added an equal volume of cold (4° C.) 0.9 M sodium chloride solution. After three hours at 4° C., the mixture was concentrated to one tenth its original volume by passing the solution through a 30,000 dalton cutoff membrane. The resulting concentrated supernatant was dialyzed against cold (4° C.) double distilled water for 24 hours. The final purified solution was filter sterilized and dried under vacuum yielding approximately 1200 mg dry weight per liter of culture.

Final quality assays, based on three batches of culture, yielded the following results: 482 mgs/l of protein; 725.6 mgs/l of carbohydrate; <0.01 mgs/l of nucleic acid.

EXAMPLE 2

Vaccine from *Pasteurella multocida*

A vaccine was prepared against *Pasteurella multocida*, Groups A and D, according to the procedures described in Experiments 1.1 and 1.2 above, except that the strains were cultured on YCC as opposed to CAM.

The final purified solution was dried under vacuum yielding approximately 1210 mg dry weight per liter of culture. Final quality assays, based on three batches of culture, yielded the following results: 1168.15 mgs/l of protein; 34.95 mgs/l of carbohydrate; <0.01 mgs/l of nucleic acid.

EXAMPLE 3

Immunization with *P. multocida* Vaccine

The vaccine of example 2 was tested on young mice. The vaccine was solubilized in sterile saline. Groups of ten mice each were injected intraperitoneally (IP) with 5.0 10 and 15 mcg of vaccine based on carbohydrate analysis and boosted with a similar dosage 7 days later. The mice were challenged seven days after the booster with $5 \times 10^5$ bacteria and death observed thereafter over a period of five days. The mortality results are reported in TABLE 3. The date of death of both groups with only 40% mortality was later by two days than the date of death in the control group.

TABLE 3

| VACCINE EFFICACY EXPRESSED AS PERCENTAGE OF DEATHS | |
| --- | --- |
| Dosage (mcg) | % Mortality |
| 0.0 (control) | 80% |
| 5.0 | 40% |
| 10.0 | 20% |
| 15.0 | 40% |

I claim:

1. A method for preparing an acellular vaccine from a culture of a pathogenic bacterium comprising the steps of:
   a. homogenizing the culture during late log-phase to release immunogenic components;
   b. separating bacteria and bacterial fragments to provide a first supernatant containing immunogenic components;
   c. adding a cationic precipitating agent to the first supernatant to form a precipitate comprising an ionic complex of the agent and the cell-derived compounds;
   d. separating the first precipitate from the first supernatant to provide a second supernatant;
   e. adding high salt solution to the second supernatant to dissociate any remaining ionic complexes;
   f. concentrating the second supernatant;
   g. dialyzing the second supernatant against double-distilled water.

2. The method of claim 1 wherein homogenization is accomplished using high speed blades.

3. The method of claim 2 wherein separation in steps (b) and (d) is accomplished by high speed centrifugation.

4. The method of claim 2 wherein the cationic precipitating agent is a mixed alkyltrimethyl ammonium bromide.

5. The method of claim 4 wherein the mixed alkyltrimethyl ammonium bromide is Cetavalon.

6. The method of claim 1 wherein the supernatant of step (f) is concentrated to one-tenth original volume.

7. The method of claim 6 wherein concentration is accomplished by passing the mixture through a cutoff membrane.

8. The method of claim 1 further comprising the step of filter sterilizing the second supernatant following dialysis against double-distilled water.

9. The method of claim 1 wherein the bacterium is selected from the group consisting of *Moraxella bovis*, Haemophilus spp., Pasteurella spp. and *Actinobacillus pleuropneumoniae*.

10. A method for preparing an acellular vaccine from a culture of a pathogenic bacterium comprising the steps of:
    a. homogenizing the culture during late log-phase using high speed blades to release immunogenic components;
    b. separating bacteria and bacterial fragments by high speed centrifugation to provide a first supernatant containing immunogenic components;
    c. adding a mixed alkyltrimethyl ammonium bromide as a cationic precipitating agent to the first supernatant to form a precipitate comprising an ionic complex of the agent and the cell-derived compounds;
    d. separating the precipitate from the first supernatant by high speed centrifugation to provide a second supernatant;
    e. adding high salt solution to the second supernatant to dissociate any remaining ionic complexes;
    f. concentrating the second supernatant by passing the supernatant through a cutoff membrane to reduce the mixture to one-tenth original volume to provide a concentrated supernatant;
    g. dialyzing the concentrated supernatant against distilled water;
    h. filter sterilizing the concentrated supernatant.

11. The method of claim 10 wherein the mixed alkyltrimethyl ammonium bromide is Cetavalon.

12. The method according to claim 11 wherein the bacterium is selected from the group consisting of *Moraxella bovis*, Haemophilus spp., Pasteurella spp. and *Actinobacillus pleuropneumoniae*.

13. A method for preparing a veterinary acellular vaccine from a culture of a pathogenic bacterium comprising the steps of:
    a. inactivating the culture during late log-phase;
    b. homogenizing the culture to release immunogenic components;
    c. separating bacteria and bacterial fragments to provide a first supernatant containing immunogenic components;
    d. adding a cationic precipitating agent to the first supernatant to form a precipitate comprising an ionic complex of the agent and the cell-derived compounds;
    e. separating the first precipitate from the first supernatant to provide a second supernatant;
    f. adding high salt solution to the second supernatant to dissociate any remaining ionic complexes;
    g. concentrating the second supernatant;
    h. dialyzing the second supernatant against double-distilled water.

14. A method for preparing a veterinary acellular vaccine from a culture of a pathogenic bacterium comprising the steps of:
    a. inactivating the culture with formaldehyde during late log-phase;
    b. homogenizing the culture using high speed blades to release immunogenic components;
    c. separating bacteria and bacterial fragments by high speed centrifugation to provide a first supernatant containing immunogenic components;
    d. adding a mixed alkyltrimethyl ammonium bromide as a cationic precipitating agent to the first supernatant to form a precipitate comprising an ionic complex of the agent and cell-derived compounds;
    e. separating the precipitate from the first supernatant by high speed centrifugation to provide a second supernatant;
    f. adding high salt solution to the second supernatant to dissociate any remaining ionic complexes;
    g. concentrating the second supernatant by passing the supernatant through a cutoff membrane to reduce the mixture to one-tenth original volume and thereby provide a concentrated supernatant;

h. dialyzing the concentrated supernatant against distilled water;

i. filter sterilizing the concentrated supernatant.

15. The method of claim 14 wherein the mixed alkyltrimethyl ammonium bromide is Cetavalon.

16. The method according to claim 15 wherein the bacterium is selected from the group consisting of *Moraxella bovis*, Haemophilus spp., Pasteurella spp. and *Actinobacillus pleuropneumoniae*.

17. A veterinary vaccine effective against pathogenic bacteria comprising a mixture of:

a. an injectable vehicle;

b. an immunogenic composition prepared from a culture of pathogenic bacteria by:

i) homogenizing the culture during late log-phase to release immunogenic components;

ii) separating bacteria and bacteria fragments to provide a first supernatant containing immunogenic components;

iii) adding a cationic precipitating agent to the first supernatant to form precipitate comprising an ionic complex of the agent and the cell-derived compounds;

iv) separating the first precipitate from the first supernatant to provide a second supernatant;

v) adding high salt solution to the second supernatant to dissociate any remaining ionic complexes;

vi) concentrating the second supernatant;

vii) dialyzing the second supernatant against double-distilled water.

18. A veterinary vaccine effective against pathogenic bacteria comprising a mixture of:

a. an injectable vehicle;

b. an immunogenic composition prepared from a late log phase culture of pathogenic bacteria by:

i) inactivating the culture with formaldehyde during late log-phase;

ii) homogenizing the culture using high speed blades to release immunogenic components;

iii) separating bacteria and bacterial fragments by high speed centrifugation to provide a first supernatant containing immunogenic components;

iv) adding a mixed alkyltrimethyl ammonium bromide as a cationic precipitating agent to the first supernatant to form a precipitate comprising an ionic complex of the agent and the cell-derived compounds;

v) separating the precipitate from the first supernatant by high speed centrifugation to provide a second supernatant;

vi) adding high salt solution to the second supernatant to dissociate any remaining ionic complexes;

vii) concentrating the second supernatant by passing the supernatant through a cutoff membrane to reduce the mixture to one-tenth original volume to provide a concentrated supernatant;

viii) dialyzing the concentrated supernatant against distilled water;

ix) filter sterilizing the concentrated supernatant.

19. The vaccine according to claim 18 wherein the bacterium is selected from the group consisting of *Moraxella bovis*, Haemophilus spp., Pasteurella spp. and *Actinobacillus pleuropneumoniae*.

* * * * *